US012377296B2

(12) United States Patent
Ferguson

(10) Patent No.: US 12,377,296 B2
(45) Date of Patent: Aug. 5, 2025

(54) SUPPORT FOR A SELF-CONTAINED BREATHING APPARATUS

(71) Applicant: DRAEGER SAFETY UK LIMITED, Blyth (GB)

(72) Inventor: Darin Ferguson, Ashington (GB)

(73) Assignee: DRAEGER SAFETY UK LIMITED, Blyth (GB)

( * ) Notice: Subject to any disclaimer, the term of this patent is extended or adjusted under 35 U.S.C. 154(b) by 891 days.

(21) Appl. No.: 17/178,731

(22) Filed: Feb. 18, 2021

(65) Prior Publication Data
US 2021/0290990 A1 Sep. 23, 2021

(30) Foreign Application Priority Data

Mar. 23, 2020 (EP) .................................... 20164985

(51) Int. Cl.
*A62B 9/04* (2006.01)
*A62B 25/00* (2006.01)
*F17C 13/08* (2006.01)
*B63C 11/02* (2006.01)

(52) U.S. Cl.
CPC ................ *A62B 9/04* (2013.01); *A62B 25/00* (2013.01); *F17C 13/084* (2013.01); *A61M 2209/084* (2013.01); *B63C 2011/026* (2013.01); *F17C 2201/0109* (2013.01); *F17C 2205/0157* (2013.01); *F17C 2205/0323* (2013.01); *F17C 2270/025* (2013.01)

(58) Field of Classification Search
CPC ..... B63C 2011/026; A62B 9/04; A62B 25/00; F17C 2270/025
See application file for complete search history.

(56) References Cited

U.S. PATENT DOCUMENTS

| 4,586,687 A * | 5/1986 | Ziaylek, Jr. ............ A62B 25/00 211/75 |
| 6,926,243 B1 * | 8/2005 | Ziaylek .................. A62B 25/00 248/307 |
| 8,196,791 B2 * | 6/2012 | Hogg ........................ A45F 3/10 224/628 |
| 8,608,040 B2 * | 12/2013 | Cheesman ............. A62B 25/00 224/628 |

(Continued)

FOREIGN PATENT DOCUMENTS

| CN | 101366992 A | 2/2009 |
| CN | 201248937 Y | 6/2009 |

(Continued)

OTHER PUBLICATIONS

European Search Report, dated Sep. 25, 2020, issued in priority European Application No. 20164985.2.

(Continued)

*Primary Examiner* — Rachel T Sippel
*Assistant Examiner* — Gwynneth L Howell
(74) *Attorney, Agent, or Firm* — Banner & Witcoff, LTD.

(57) ABSTRACT

A support for a breathing apparatus including a cylinder cradle with a retaining surface for retaining a cylinder of compressed gas and a cylinder glider including a gliding element, the gliding element configured to support the cylinder above the retaining surface, wherein the cylinder glider is longitudinally separated from the retaining surface of the cylinder cradle.

19 Claims, 4 Drawing Sheets

(56) References Cited

U.S. PATENT DOCUMENTS

| | | | |
|---|---|---|---|
| 8,622,268 B2* | 1/2014 | Townsend | A62B 25/00 224/633 |
| 8,622,469 B2* | 1/2014 | Hogg | B60R 11/00 248/316.5 |
| 9,212,784 B2* | 12/2015 | Frenal | F17C 13/084 |
| 2002/0078959 A1* | 6/2002 | Haeuser | A62B 9/04 128/205.22 |
| 2005/0035258 A1 | 2/2005 | Kling et al. | |
| 2008/0179367 A1* | 7/2008 | Storey | A45F 3/10 224/642 |
| 2009/0045657 A1 | 2/2009 | Bostrom et al. | |
| 2011/0048421 A1* | 3/2011 | Carr | B63C 11/02 224/633 |
| 2014/0069427 A1* | 3/2014 | Farnaby | A62B 9/04 128/204.18 |
| 2015/0144137 A1* | 5/2015 | Losos | A62B 25/00 248/311.2 |
| 2015/0144674 A1* | 5/2015 | Losos | A62B 9/04 224/633 |

FOREIGN PATENT DOCUMENTS

| | | |
|---|---|---|
| CN | 101879360 A | 11/2010 |
| CN | 103656905 A | 3/2014 |
| CN | 104027904 A | 9/2014 |
| CN | 205198735 U | 5/2016 |
| CN | 105764574 A | 7/2016 |
| CN | 107823817 A | 3/2018 |
| CN | 110101986 A | 8/2019 |
| GB | 0407795 | 5/2004 |

OTHER PUBLICATIONS

Search Report, dated Jul. 14, 2023, issued in related Chinese Application No. 2021103027097.

* cited by examiner

SUPPORT FOR A SELF-CONTAINED BREATHING APPARATUS

CROSS-REFERENCE TO RELATED APPLICATIONS

This application claims priority to European Application No. 20164985.2, filed on Mar. 23, 2020, the entire contents of which being fully incorporated herein by reference.

The disclosure relates to a support for a breathing apparatus.

BACKGROUND

A typical support for a breathing apparatus, such as a self-contained breathing apparatus (SCBA), comprises a frame configured for attachment to the back of a user, and a cylinder support on which a breathing gas cylinder can be secured.

After a breathing gas cylinder has been exhausted, it must be replaced. In an emergency situation, it is desirable that a breathing gas cylinder can be installed and/or replaced rapidly.

It is therefore desirable to provide an improved support arrangement.

BRIEF DESCRIPTION OF THE INVENTION

According to an aspect, there is provided a support for a breathing apparatus comprising: a cylinder cradle comprising a retaining surface for retaining a cylinder of compressed gas; and a cylinder glider comprising a gliding element, the gliding element configured to support the cylinder above the retaining surface; wherein the cylinder glider is longitudinally separated from the retaining surface of the cylinder cradle.

The support may be a back plate of a breathing apparatus, such as a self-contained breathing apparatus. The principles of this disclosure may be equally applied to other breathing apparatuses, such as closed-circuit breathing apparatuses having replaceable gas cylinders.

The cylinder glider may enable easy installation, removal and/or replacement of the cylinder. By locating the glider separately from the cradle, rather than as part of the cradle, the surface area of the cradle for contact with the cylinder can be maximised. The support may be used with cylinders of a range of dimensions. Longitudinal separation does not necessarily mean that there is a space between the cradle and glider. The cradle and glider may be immediately adjacent each other in a longitudinal direction.

The support may be configured to be arranged on a user's back. The support may be arranged, in use, so as to overlie a user's back. The support may extend in a longitudinal direction. The longitudinal direction may be, in use, a substantially vertical direction. The longitudinal direction may be substantially parallel to the direction of extension of a user's spine. The support may be configured for installation of a gas cylinder in the longitudinal direction. The support may be a backplate.

The retaining surface may comprise a gripping surface. The retaining surface may have a high coefficient of friction with a cylinder such that the cylinder is not able to easily slide over the retaining surface. The retaining surface may have a generally concave circular form so as to conform to the periphery of a cylinder of compressed gas. The retaining surface may allow full contact with the cylinder and provide a secure connection which is resilient to impact and vibration.

The gliding element may comprise a gliding surface. The gliding surface may comprise a gliding protrusion. The gliding surface may comprise a plurality of gliding protrusions. The gliding element may have a low coefficient of friction with a cylinder such that the cylinder is able to glide freely along the gliding element. The cylinder glider may comprise a plurality of gliding elements.

The gliding element may be configured to support the cylinder above the retaining surface, such that the cylinder is raised relative to the retaining surface. The gliding element may be configured to support the cylinder above the retaining surface, such that the cylinder is proud of the retaining surface. The gliding element may be configured to support the cylinder above the retaining surface such that, when installing a cylinder on the support, the contact between the cylinder and the retaining surface is reduced, such that the position of the cylinder can be adjusted more easily.

The gliding element may be configured to sit proud of the retaining surface. It should be understood that this means that the gliding element may be raised relative to the retaining surface. The gliding element may protrude relative to the retaining surface. The gliding element may generally be configured to contact a cylinder during its attachment to the support and space the cylinder apart from the receiving surface, so as to inhibit the cylinder from contacting the receiving surface.

The glider may extend laterally across the support. The gliding element may extend laterally across the support. The gliding element may comprise a gliding surface which extends laterally across the support.

The gliding element may be moveable between a) a gliding position in which the gliding element sits proud of the retaining surface and the support surface; and b) a retracted position in which the gliding element is flush with, or retracted below the retaining surface. The gliding element may be depressible into the retracted position. The gliding element may be compressible into the retracted position.

The support may further comprise means for clamping a cylinder (i.e. urging a cylinder against the retaining surface). This may allow the cylinder to be fixed in position for use, and to be released after use. The gliding element may be configured to be moved into the retracted position by the clamping of a cylinder on the support, (i.e. by a force applied on the gliding element by the cylinder from the action of the clamping means). The means for clamping a cylinder may comprise a generally circular band through which a cylinder can be passed, and which can be tightened to clamp the cylinder against the retaining surface. The circular band may be adjustable such that the support can accommodate cylinders of different dimensions. The means for clamping a cylinder may comprise a cylinder strap and adjustable buckle arrangement.

The cylinder glider may be resiliently deformable so as to move the gliding element between the gliding position and the retracted position. The cylinder glider may be hinged so as to provide the resilient deformability. The cylinder glider may comprise a resiliently deformable material. The gliding element may be resiliently deformable. The gliding element may comprise a resiliently deformable material. The material may be conductive. The material may be flame retardant. The material may provide a good combination of strength, resilience, self-lubricating properties and an appropriate flexural modulus so as to provide a high degree of flex without plastic deformation. The material may further comprise fillers and/or additives. The material may be electrostatically dissipating. The material may have reduced surface resistivity. The material may have modified impact properties. Filler, conductive additives, or flame-retardant additives may be added to the material to enhance the properties. The glider may be manufactured from a polymeric material. The glider may be manufactured from polyamide 6, or polyamide 6/6. The glider may be manufactured from polyamide 6, or polyamide 6/6 comprising 10% carbon fibres and 25% glass fibres.

The support may comprise longitudinally spaced first and second ends, the second end comprising a pressure reducer valve. The cylinder glider may be positioned between the cylinder cradle and the first end. The cylinder glider may be positioned on the opposite side of the cylinder cradle to the pressure reducer valve. During installation of a cylinder, the cylinder may contact the cylinder glider before contacting the cylinder cradle.

The gliding element may be arranged so as to guide the cylinder into a central position on the support. This may provide a self-aligning feature of the support. The gliding element may be a guiding element. The guiding element may comprise a concave surface for contact with the gas cylinder. The gliding element may be arranged centrally on the support.

The gliding element may have a lower coefficient of friction than the retaining surface. This may allow the cylinder to more easily slide along the gliding element than the retaining surface. This may allow for ease of insertion of a cylinder.

The cylinder glider may be immediately adjacent the cylinder cradle. This may provide a compact arrangement of the glider and cradle on the support. The closer the cylinder glider is to the cylinder cradle, the smaller the contact area between the cylinder and the cradle.

The cylinder glider may be removably attached to the support. This may enable use of the support with or without the glider. Easy removal may enable ease of cleaning or maintenance of the glider and the support. Furthermore, the glider may be easily replaced if it is damaged without replacing the entire support.

The cylinder glider may comprise a plurality of gliding elements for contacting the cylinder. The gliding elements may be spaced laterally. The cylinder glider may comprise 3 gliding elements. The shape, location and dispersion of the gliding elements may be selected to provide guiding of a cylinder on installation. The shape, location and dispersion of the gliding elements may be selected to provide self-alignment of a cylinder on installation. The gliding elements may be located substantially symmetrically about a central longitudinal axis of the support.

The cylinder cradle may comprise a resiliently deformable material. The retaining surface may comprise a resiliently deformable material. The cylinder cradle may be conductive. The cylinder cradle may be flame retardant. The cylinder cradle may be self-extinguishing. The cylinder cradle may be formed from an elastomeric material. The cylinder cradle may formed from a rubber. The cylinder cradle may be formed from Chloroprene rubber. The material may be carbon loaded to provide improved electrical conductive properties. Chloroprene rubber may provide good resistance to ozone cracking, heat aging and chemical attack.

According to a further aspect there is provided a breathing apparatus, optionally a self-contained breathing apparatus, comprising a support according to the first aspect described above.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

BRIEF DESCRIPTION OF THE FIGURES

Embodiments of the present invention relate to will now be described by way of example only, with reference to the Figures, in which.

DETAILED DESCRIPTION OF THE FIGURES

Figure 1:
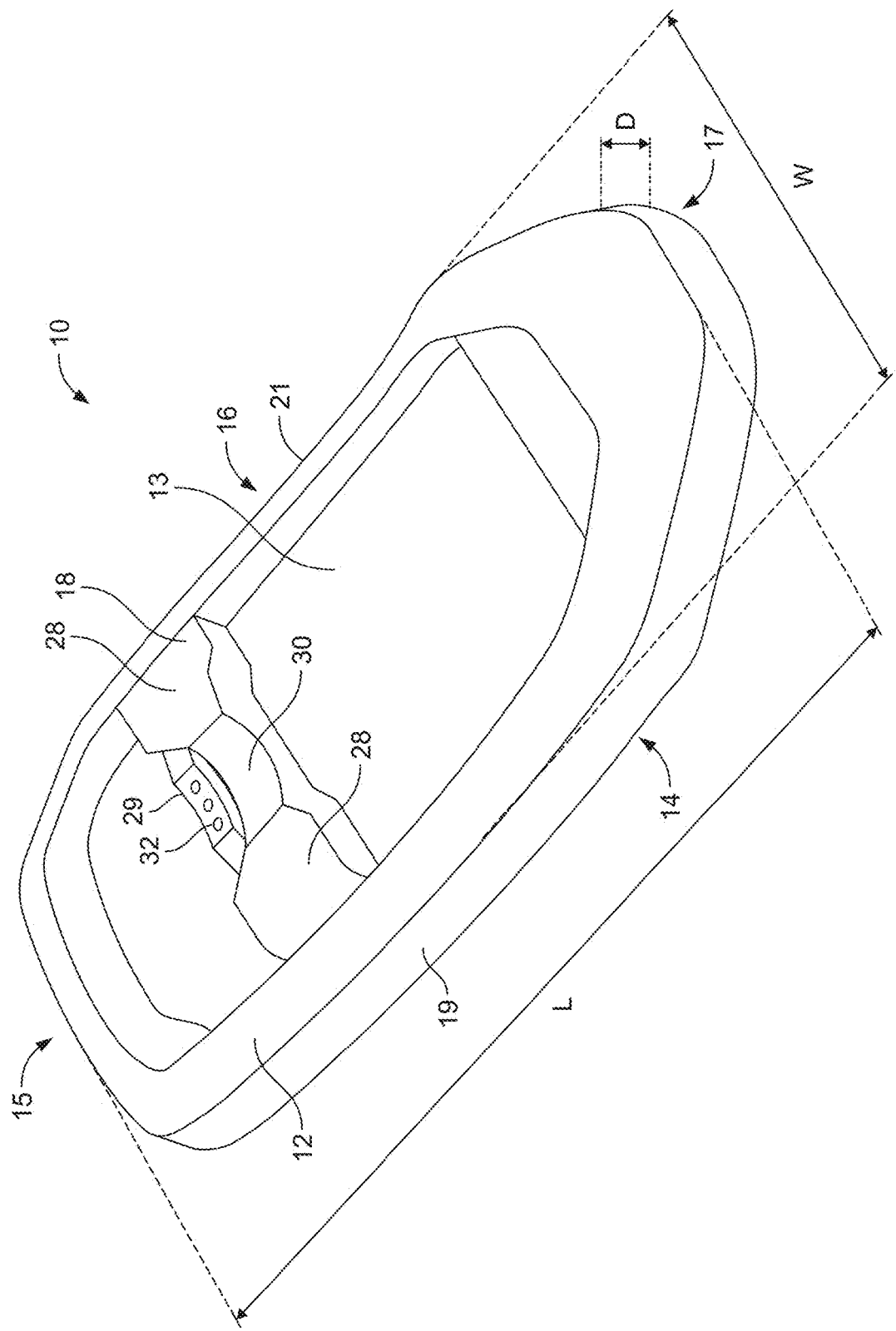
FIG. 1 schematically shows a perspective view of a support for a breathing apparatus according to the present invention.

With reference to FIG. 1, the support 10 for a breathing apparatus comprises a substantially rectangular structural frame 12 defining a central opening 13. The support 10 comprises an inner side 14, an outer side 16, an upper end 15, a lower end 17, a left side 19 and a right side 21. The frame 12 extends in a longitudinal direction between the upper end 15 and the lower end 17, defining a length L. The frame 12 extends in a lateral direction between the left side 19 and the right side 21, defining a width W. The frame 12 extends in a depth direction between the inner side 14 and the outer side 16, defining a depth D. In use, the inner side 14 is arranged adjacent to a user's back, and the outer side 16 faces away from a user's back. Straps (not shown) may be provided to permit a user to don the support 10 on their back.

Figure 2:
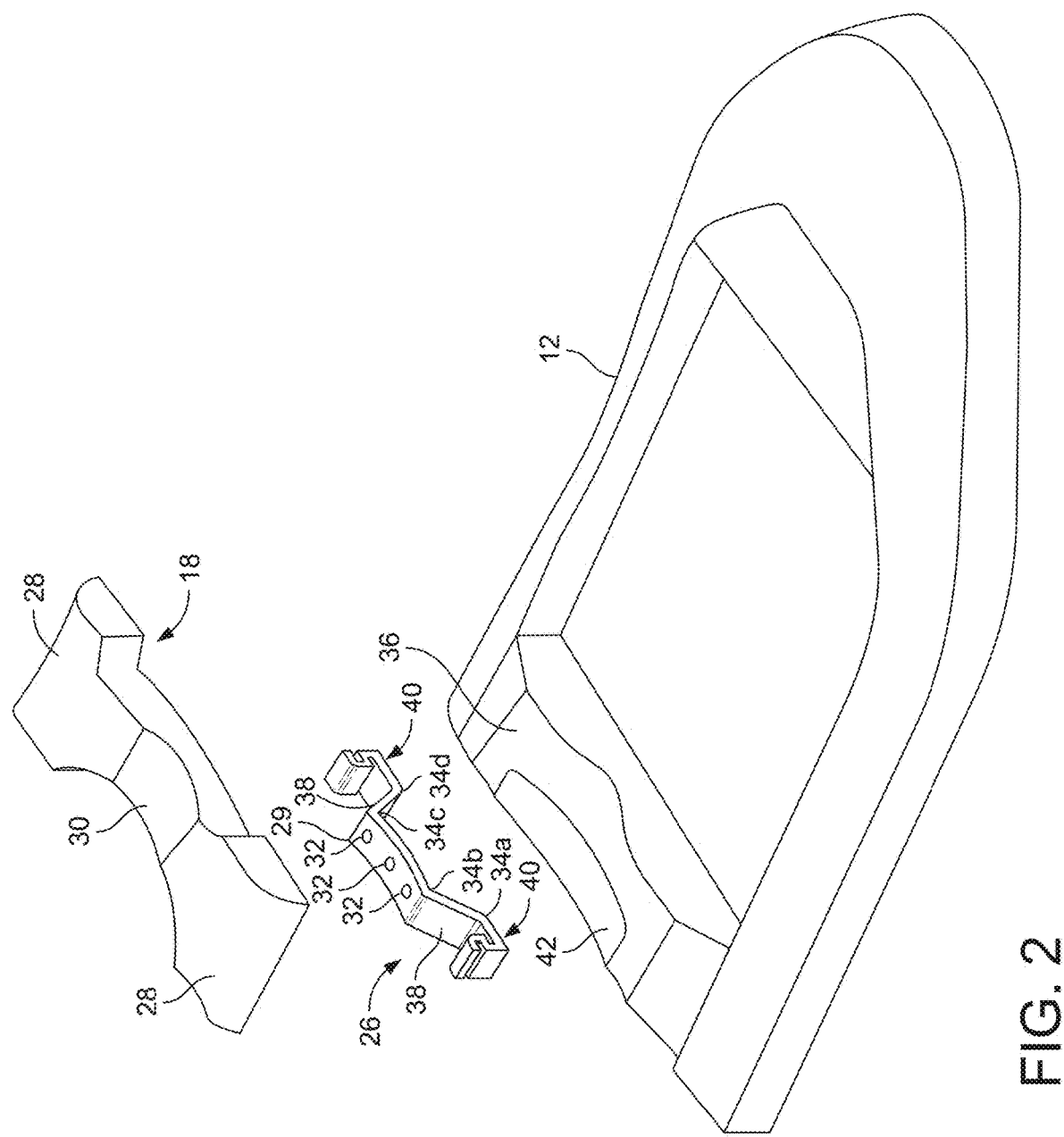
FIG. 2 schematically shows an exploded perspective view of the support of FIG. 1.

As can be seen in FIG. 2, the frame 12 further comprises a laterally extending bridge portion 36, to which a cylinder glider 26 and a cylinder cradle 18 may be removably attached on an outer side 16 of the support (as will be discussed below). The support 10 further comprises a cylinder clamping band 20 (shown in FIG. 4). The clamping band 20 comprises an adjustable loop which can be tightened around the cylinder 22.

Figure 3:
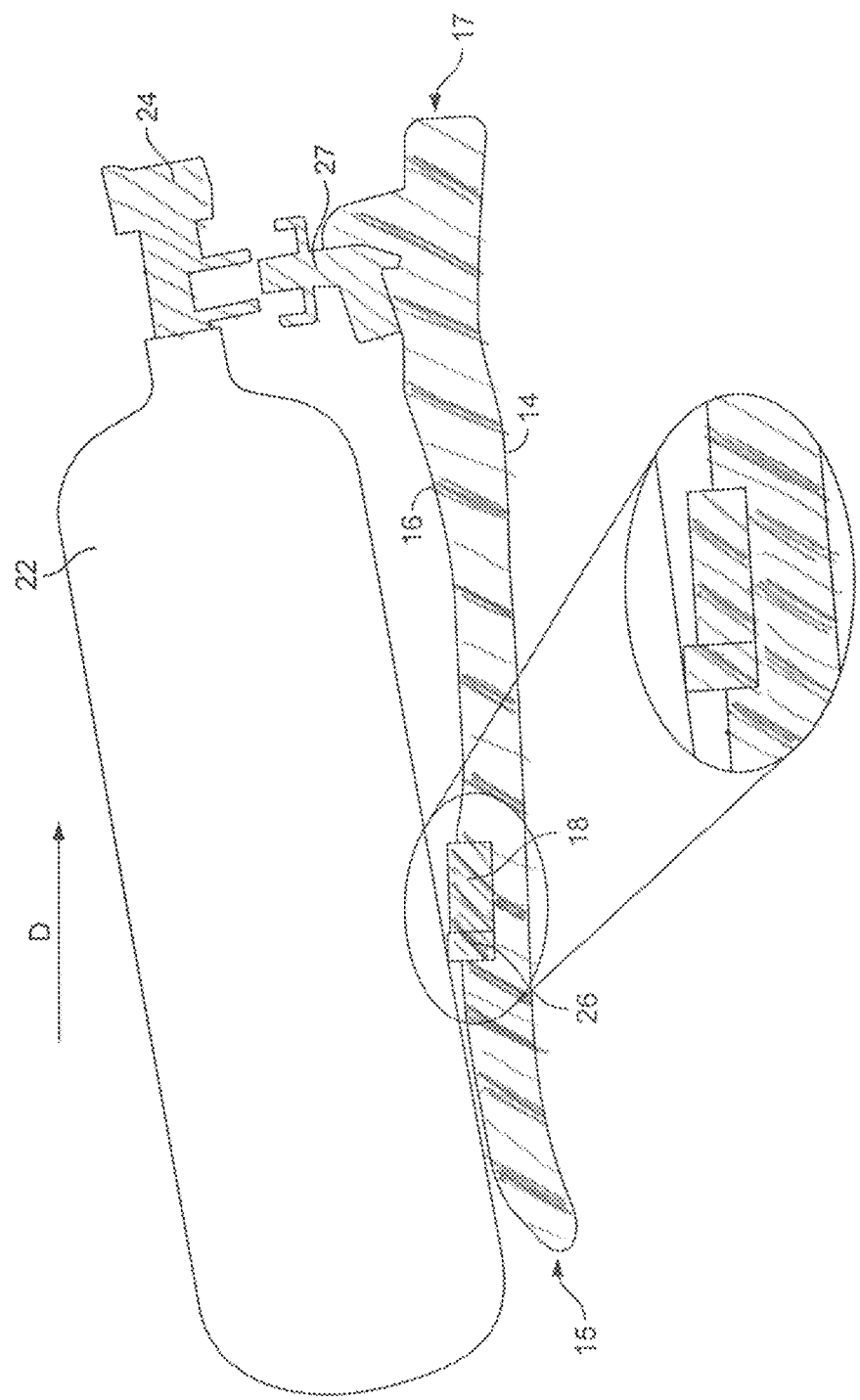
FIG. 3 schematically shows a side cross-sectional view of the support of FIGS. 1 and 2 taken along line A-A in FIG. 1, showing a glider in a gliding position and also including a gas cylinder (also shown in cross-section)
Figure 4:
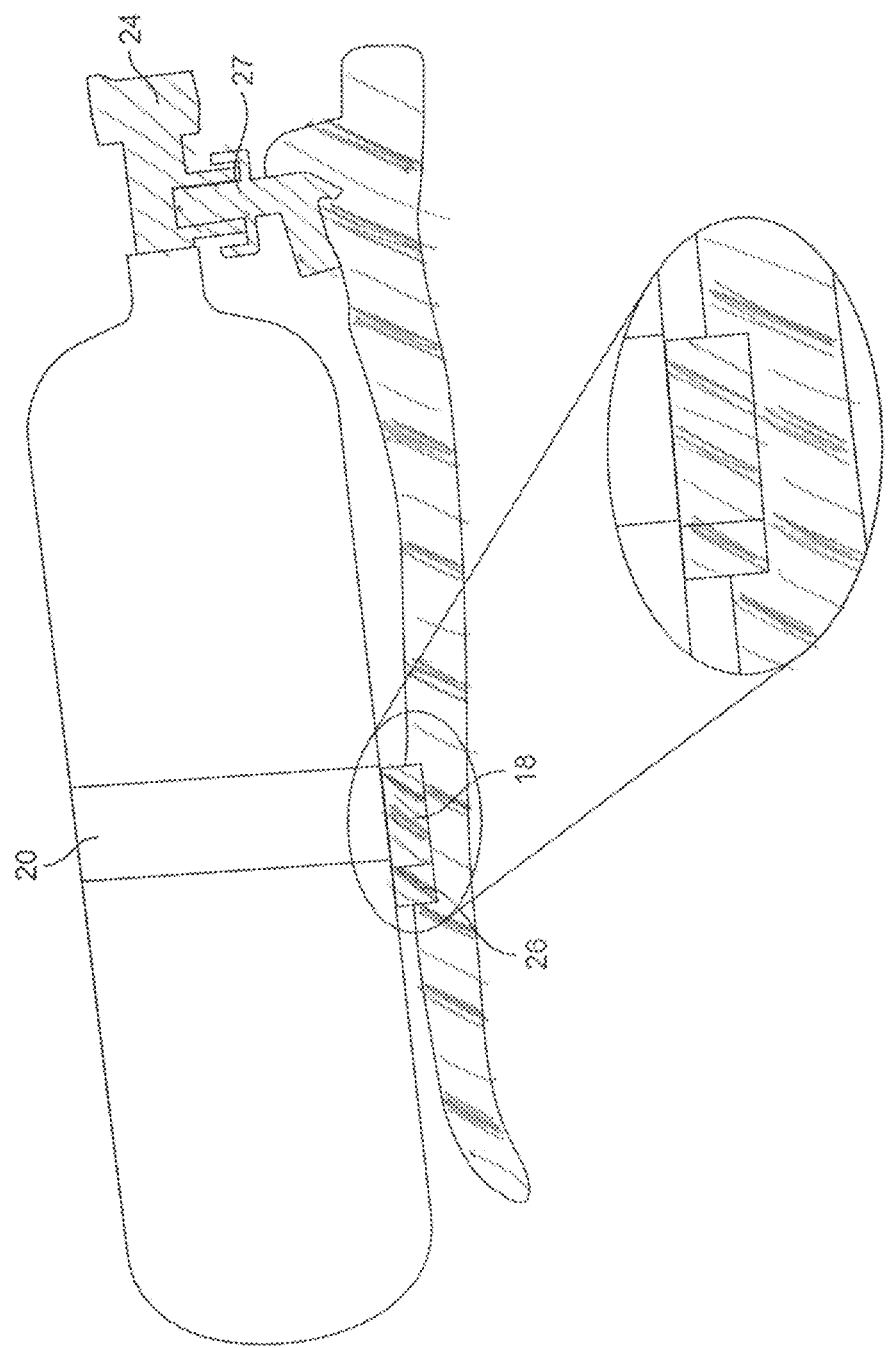
FIG. 4 schematically shows a side cross-sectional view of the support of FIGS. 1 and 2 taken along line A-A in FIG. 1, showing a glider in a retracted position and also including a gas cylinder (also shown in cross-section).

The cylinder cradle 18, removably attached on an outer side 16 of the support, comprises two shoulder portions 28 and a retaining surface, in this embodiment, a central saddle 30. It will be appreciated that the invention is not limited to the saddle as hereindefined, and that other arrangements of the retaining surface may be contemplated by the skilled person. The cradle 18 extends laterally across the central opening 13 of the frame 12. The cradle 18 is located approximately one-third of the length L from the upper end 15 to the lower end 17. A gas cylinder 22 can be installed onto the support 10 in a direction D extending from the upper end 15 to the lower end 17, and supported on the cradle 18 and held in place by the clamping band 20. As shown in FIGS. 3 and 4, the outer side 16 further comprises a pressure reduction valve 27 towards the lower end 17, which is configured to connect with a cylinder valve 24 on the cylinder 22 in order to provide gas flow from the cylinder 22, via the valves 24, 27 to a user's breathing mask (not shown). The skilled person will appreciate that the gas cylinder 22 may also be inserted in the opposite direction (i.e. from the lower end to the upper end), and achieve some benefits of the invention as discussed throughout this application.

The saddle 30 has a concave circular form, which is generally conformable to the periphery of a cylinder 22, to ensure full contact is maintained with the cylinder 22 when the cylinder 22 is clamped to the support 10 with the clamping band 20. The saddle 30 is manufactured from a resiliently deformable elastomeric material, in this example Chloroprene rubber. The material comprises a conductive additive, in this example carbon. The conductive additive improves the properties of the material for use in explosive environments. Further additives may increase the stiffness and tensile strength of the material.

The support 10 is configured for attachment to a user's back via a strap arrangement (not shown), which can be attached to the support 10 at strap fixing points on the inner side 14 of the frame 12. The strap arrangement can be placed over a user's shoulders such that the support 10 can be supported on a user's back.

The support 10 further comprises a cylinder glider 26 located on the outer side 16, and longitudinally separated from the cradle 18. The glider 26 extends laterally across the support 10. In this embodiment, the glider 26 is located immediately adjacent an upper side of the cradle 18 (i.e. towards the upper end 15 of the frame 12, on the opposite side of the cradle 18 to the pressure reduction valve 27). In other embodiments, the glider 26 may be located immediately adjacent a lower side of the cradle 18 (i.e. between the cradle 18 and the pressure reduction valve 27), or may be spaced further apart from the upper or lower side of the cradle 18.

The glider 26 comprises a gliding element, in this embodiment a gliding surface 29 defining three gliding protrusions 32. The gliding surface 29 extends laterally across the glider. The gliding protrusions 32 are spaced laterally across the gliding surface 29. The glider 26 is hinged at four positions 34a, 34b, 34c, 34d so that the gliding surface 29 (and therefore the gliding protrusions 32) can be resiliently deformed in the depth direction. In other embodiments, the glider 26 may comprise a resiliently deformable material in order to provide the resilient deformability in the depth direction. In further embodiments, the glider 26 may comprise a gliding surface 29 supported by a leaf or compression spring arrangement below the gliding surface, so as to be resiliently deformable in the depth direction. The resilient deformability of the glider 26 in the depth direction allows the glider 26 to be moved between a gliding position and a retracted position. The gliding surface 29 and gliding protrusions 32 are biased into the gliding position.

In the gliding position (FIG. 3), the gliding protrusions 32 of the gliding surface 29 protrude outwardly of the saddle 30 in a depth direction. In other words, a distance between the gliding protrusions 32 of the gliding surface 29 and the frame 12 in a depth direction is greater than a distance between the saddle 30 and the frame 12 in a depth direction. This arrangement means that during installation of a cylinder 22 onto the support 10, the cylinder 22 is held away from the saddle 30 due to the contact with the gliding protrusions 32 of the gliding surface 29, as will be discussed below. By reducing contact with the saddle 30 during installation, ease of installation of the cylinder 22 can be improved.

In the retracted position (FIG. 4), the gliding protrusions 32 of the gliding surface 29 are deformed in the depth direction, towards the support 10, such that the gliding protrusions 32 are level with the saddle 30. In other words, the distance between the gliding protrusions 32 and the frame 12 in a depth direction is the same as the distance between the saddle 30 and the frame 12 in a depth direction. This means that after installing the cylinder 22 onto the support 10, the gliding protrusions 32 of the gliding surface 29 can be retracted away (or lowered) such that full contact between the cylinder 22 and saddle 30 can be effected. This provides an arrangement in which the cylinder 22 is securely held in position by contact with the saddle 30, and provides resilience to impact and vibration.

As discussed above, the gliding surface 29 defines three gliding protrusions 32. The gliding protrusions 32 are evenly spaced across the width of the gliding surface 29. The gliding protrusions 32 are raised above the saddle 30 in a gliding position. The gliding protrusions 32 have a planar surface, but in other embodiments may be slightly curved so as to conform to the outer surface of a cylinder 22, or may be hemispherical to provide point contact only. The gliding protrusions 32 provide a low-friction surface which allows a cylinder 22 to easily slide over the gliding protrusions 32. The gliding protrusions 32 are arranged symmetrically about the longitudinal axis of the support 10 so as to provide a self-aligning feature for the cylinder 22. For example, the two outer gliding protrusions 32 are configured to provide contact and guiding with larger diameter cylinders, and the central gliding protrusion 32 is configured to contact a smaller diameter cylinder, with guiding provided by the outer gliding protrusions 32. The shape, height and dispersion of the gliding protrusions 32 can be adjusted to tailor the aligning feature.

The gliding protrusions 32 and the gliding surface 29 comprise a polymeric material such as Polyamide 6 or Polyamide 6/6. The Polyamide 6 or Polyamide 6/6 further comprises 10% carbon fibres and 25% glass fibres. These materials provide a good combination of strength, resilience, self-lubricating properties and an appropriate flexural modulus so as to provide a high degree of flex without plastic deformation. Other materials may be contemplated by the skilled person. Filler, conductive additives, or flame-retardant additives can be added to the material to enhance the properties if necessary. Example materials properties are: flexural modulus of 9500 MPa and flexural strength of 200 MPa. It will be appreciated that a range of materials properties will be appropriate for the gliding protrusions 32 and gliding surface 29.

In this embodiment, the gliding surface 29 comprises three gliding protrusions 32. In other embodiments it will be appreciated that the gliding surface 29 may comprise a different number of gliding protrusions 32. In an embodiment where only a single gliding protrusion 32 is provided, the gliding protrusion 32 may be centrally located on the gliding surface 29. The gliding protrusion 32 may have a planar surface, but in other embodiments may be slightly curved so as to conform to the outer surface of a cylinder 22, or may be hemispherical to provide point contact only. A curved surface may act to guide a cylinder 22 into a central position during installation.

As mentioned above, and as shown in FIG. 2, the glider 26 and cradle 18 are removably attached to the frame 12 at the bridge portion 36 of the frame 12. The cradle 18 is attached to the bridge portion 36 by the engagement of barbs on the cradle (not shown) with corresponding slots in the bridge portion 36 (not shown), however other means of attachment will be contemplated by the skilled person.

The glider 26 comprises resilient arms 38 and locking tabs 40. The resilient arms 38 can be deformed inwardly in a lateral direction, by action of the hinges 34b, 34c upon application of an inward force to the arms. This reduces the width of the glider 26, such that the glider 26 can be inserted into a corresponding opening 42 of the bridge portion 36. Upon release of the arms 38, the glider 26 reverts to its original extended position. The tabs 40 cooperate with the periphery of the opening 42 in order to lock the glider 26 into position.

In use, a cylinder 22 is installed on the support 10 by moving the cylinder 22 in the direction D from the upper end 15 to the lower end 17 of the support 10, passing the cylinder 22 through the clamping band 20. During this movement, as the glider 26 is in the gliding position, raised above the saddle 30 of the cradle 18, the cylinder 22 contacts the glider 26 as shown in FIG. 3. The glider 26 has a lower coefficient of friction with the cylinder 22 than the coefficient of friction between the cradle 18 and the cylinder 22, and also has a smaller surface area in contact with the cylinder 22. The cylinder 22 therefore easily glides along the glider 26 with minimal contact with the cradle 18. The arrangement of the gliding protrusions 32 on the glider 26 guides the cylinder 22 so that it is centrally located on the width of the support 10. The cylinder valve 24 is then connected to the reducer valve 27 on the support 10 (as shown in FIG. 4), and the clamping band 20 is tightened around the cylinder 22. During this connection, the cylinder 22 applies a force on the glider 26 which moves the glider 26 into the retracted position. With the glider 26 in the retracted position, the cylinder 22 is able to fully contact the saddle 30 of the cradle 18, thereby providing a secure and resilient connection of the cylinder 22 to the support 10 for cylinders of varying sizes. It will be appreciated by the skilled person that the glider 26 also helps with removal of the cylinder, as upon release of the clamping band 20, the glider 26 will raise, thereby raising the cylinder and reducing the amount of cylinder surface area in contact with the saddle of the cradle 18.

Although in this embodiment, gliding protrusions 32 of the gliding surface 29 are deformed by the cylinder 22 to the retracted position, resulting in the gliding protrusions 32 being level with the saddle 30, it will be appreciated that, in other embodiments, the gliding protrusions 32 may be deformable to be lower than the saddle 30, such that there is no contact between the gliding protrusions 32 and the cylinder in the retracted position. For example, the gliding protrusions 32 may be retracted into the glider 26 or the lateral bridge portion 36 of the frame 12. A separate mechanism may be provided to move the gliding protrusions 32 into the glider 26 or the frame 12, i.e. the movement of the glider 26 into the retracted position may be independent of the installation of a cylinder 22.

For the avoidance of doubt, the present disclosure extends to the subject matter in the following numbered Paras:

Para 1. A support for a breathing apparatus comprising:
  a cylinder cradle comprising a retaining surface for retaining a cylinder of compressed gas; and
  a cylinder glider comprising a gliding element, the gliding element configured to support the cylinder above the retaining surface;
  wherein the cylinder glider is longitudinally separated from the retaining surface of the cylinder cradle.

Para 2. A support according to Para 1, wherein the gliding element is configured to sit proud of the retaining surface.

Para 3. A support according to Para 1 or 2, wherein the glider extends laterally across the support.

Para 4. A support according to any preceding Para wherein the gliding element is moveable between:
  a) a gliding position in which the gliding element sits proud of the retaining surface; and
  b) a retracted position in which the gliding element is flush with the retaining surface, or retracted below the retaining surface.

Para 5. A support according to Para 4, the support further comprising means for clamping a cylinder, wherein the gliding element is configured to be moved into the retracted position by the clamping of a cylinder on the support.

Para 6. A support according to Para 4 or 5, wherein the cylinder glider is resiliently deformable so as to move the gliding element between the gliding position and the retracted position.

Para 7. A support according to Para 6, wherein the cylinder glider is hinged to provide the resilient deformability.

Para 8. A support according to any preceding Para, wherein the support comprises longitudinally spaced first and second ends, the second end comprising a pressure reducer valve, and wherein the cylinder glider is positioned between the cylinder cradle and the first end.

Para 9. A support according to any preceding Para, wherein the gliding element is arranged so as to guide the cylinder into a central position on the support.

Para 10. A support according to any preceding Para, wherein the gliding element has a lower coefficient of friction than the retaining surface.

Para 11. A support according to any preceding Para, wherein the cylinder glider is immediately adjacent the cylinder cradle.

Para 12. A support according to any preceding Para, wherein the cylinder glider is removably attached to the support.

Para 13. A support according to any preceding Para, wherein the cylinder glider comprises a plurality of gliding elements for contacting the cylinder.

Para 14. A support according to any preceding Para, wherein the cylinder cradle comprises a resiliently deformable material.

Para 15. A breathing apparatus, optionally a self-contained breathing apparatus, comprising a support as recited in any preceding Para.

The invention claimed is:

1. A wearable support for a breathing apparatus comprising:
  a structural frame extending in a longitudinal direction substantially parallel to the back of a wearer during use;
  a cylinder cradle comprising a retaining surface for retaining a cylinder of compressed gas; and
  a cylinder glider comprising a gliding element including at least one resilient arm, the gliding element configured to support the cylinder above the retaining surface, and to separate the cylinder from the retaining surface of the cylinder cradle and prevent the cylinder from directly contacting the retaining surface of the cylinder cradle;
  wherein the cylinder glider is separated from the retaining surface of the cylinder cradle in a direction longitudinal to the structural frame;
  wherein the glider extends across the entire width of the structural frame.

2. The wearable support according to claim 1 wherein the gliding element is moveable between:
   a) a gliding position in which the gliding element sits proud of the retaining surface; and
   b) a retracted position in which the gliding element is flush with the retaining surface, or retracted below the retaining surface.

3. The wearable support according to claim 2, the structural frame further comprising means for clamping the cylinder, wherein the gliding element is configured to be moved into the retracted position by the clamping of the cylinder on the support.

4. The wearable support according to claim 2, wherein the cylinder glider is resiliently deformable so as to move the gliding element between the gliding position and the retracted position.

5. The wearable support according to claim 4, wherein the cylinder glider is hinged to provide the resilient deformability.

6. The wearable support according to claim 1, wherein the structural frame further comprises longitudinally spaced first and second ends, the second end comprising a pressure reducer valve, and wherein the cylinder glider is positioned between the cylinder cradle and the first end.

7. The wearable support according to claim 1, wherein the gliding element is arranged so as to guide the cylinder into a central position on the structural frame.

8. The wearable support according to claim 1, wherein the gliding element has a lower coefficient of friction than the retaining surface.

9. The wearable support according to claim 1, wherein the cylinder glider is immediately adjacent the cylinder cradle.

10. The wearable support according to claim 1, wherein the cylinder glider is removably attached to the structural frame.

11. A wearable support according to claim 1, wherein the cylinder glider comprises a plurality of gliding elements for contacting the cylinder.

12. The wearable support according to claim 1, wherein the cylinder cradle comprises a resiliently deformable material.

13. A wearable support for a breathing apparatus, comprising:
    a structural frame extending in a longitudinal direction substantially parallel to the back of a wearer during use;
    a cylinder cradle comprising a retaining surface for retaining a cylinder of compressed gas;
    a cylinder glider including at least one resilient arm;
    wherein the cylinder glider is separated from the retaining surface of the cylinder cradle in a direction longitudinal to the structural frame
    wherein the cylinder glider comprises a concave surface.

14. The wearable support of claim 1, wherein the cylinder glider comprises a concave surface.

15. The self-contained breathing apparatus of claim 13, wherein the cylinder glider extends across the entire width of the structural frame.

16. A wearable support for a breathing apparatus, comprising:
    a structural frame extending in a longitudinal direction substantially parallel to the back of a wearer during use;
    a cylinder cradle comprising a retaining surface for retaining a cylinder of compressed gas;
    a cylinder glider including at least one resilient arm;
    wherein the cylinder glider is separated from the retaining surface of the cylinder cradle in a direction longitudinal to the structural frame;
    where the cylinder glider is in direct contact to the cylinder cradle.

17. A self-contained breathing apparatus comprising the wearable support according to claim 1.

18. A self-contained breathing apparatus comprising the wearable support according to claim 13.

19. A self-contained breathing apparatus comprising the wearable support according to claim 16.

* * * * *